(12) United States Patent
Ivaska et al.

(10) Patent No.: US 7,687,464 B2
(45) Date of Patent: Mar. 30, 2010

(54) METHOD FOR ACTIVATING T CELL PROTEIN TYROSINE PHOSPHATASE FOR THERAPEUTIC APPLICATIONS

(75) Inventors: Johanna Ivaska, Turku (FI); Elina Mattila, Nousiainen (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 473 days.

(21) Appl. No.: 11/601,847

(22) Filed: Nov. 20, 2006

(65) Prior Publication Data

US 2007/0116673 A1    May 24, 2007

Related U.S. Application Data

(63) Continuation-in-part of application No. PCT/FI2005/000203, filed on May 2, 2005.

(60) Provisional application No. 60/576,029, filed on Jun. 2, 2004.

(51) Int. Cl.
*A61K 38/08*   (2006.01)
*C07K 16/30*   (2006.01)
*C12Q 1/42*    (2006.01)
*G01N 33/574*  (2006.01)

(52) U.S. Cl. .................. 514/15; 530/328; 530/387.7; 435/21; 435/7.23

(58) Field of Classification Search .............. None
See application file for complete search history.

(56) References Cited

FOREIGN PATENT DOCUMENTS

| | | | |
|---|---|---|---|
| WO | WO 97/04133 A1 | | 2/1997 |
| WO | WO 99/16465 A1 | | 4/1999 |
| WO | WO 02/10217 | * | 2/2002 |
| WO | WO 02/10217 A2 | | 2/2002 |

OTHER PUBLICATIONS

[Retreived from] http://en.wikipedia.org/wiki/Receptor_tyrosine_kinase, 2009, 5 pages [retrieved on Apr. 11, 2009].*
[Retreived from]:http://www.cancer.gov/cancertopics/what-is-cancer, 3 page, 2009,[retrieved on Apr. 11, 2009].*
Traxler, 2003, Expert Opin. Ther. Targets, 7, 215-234.*
Schwarze, 2000, Trends in cell biology, 10, 290-295.*
Briesewitz, R., et al., "Expression of Native and Truncated Forms of the Human Integrin $\alpha_1$ Subunit", The Journal of Biological Chemistry, vol. 268, No. 4, Feb. 5, 1993, pp. 2989-2996.
Mattila, E., et al., "Negative Regulation of EGFR Signalling Through Integrin-$\alpha_1\beta_1$-Mediated Activation of Protein Tyrosine Phosphatase TCPTP", Nature Cell Biology, vol. 7, No. 1, Jan. 2005, pp. 78-85 & Supp. Information (4 pp.).

* cited by examiner

*Primary Examiner*—Andrew D Kosar
*Assistant Examiner*—Satyanarayana R Gudibande
(74) *Attorney, Agent, or Firm*—Rothwell, Figg, Ernst & Manbeck pc

(57) ABSTRACT

This invention relates to methods for activation of T cell protein tyrosine phosphatase (TCPTP) and for inhibiting tyrosine kinase signalling in an individual. The invention concerns a method for preventing or treating a disease or disorder in an individual, wherein said disease or disorder is curable by inhibiting tyrosine kinase signalling, and a method for preventing cancer, or preventing or inhibiting cancer growth, invasion or metastasis in an individual, based on activating T cell protein tyrosine phosphatase (TCPTP). The invention also concerns pharmaceutical compositions useful in the methods.

15 Claims, 19 Drawing Sheets

SEQUENCE LISTING

<160> NUMBER OF SEQ ID NOS: 9

<210> SEQ ID NO 1
<211> LENGTH: 9
<212> TYPE: PRT
<213> ORGANISM: Homo sapiens

<400> SEQUENCE: 1

Arg Pro Leu Lys Lys Met Glu Lys
1               5

<210> SEQ ID NO 2
<211> LENGTH: 27

```
<212> TYPE: PRT
<213> ORGANISM: Artificial
<220> FEATURE:
<223> OTHER INFORMATION: fusion protein

<400> SEQUENCE: 2

Tyr Gly Arg Lys Lys Arg Arg Gln Arg Arg Trp Lys Leu Gly Phe
1               5                   10                  15

Phe Lys Arg Pro Leu Lys Lys Lys Met Glu Lys
            20                  25

<210> SEQ ID NO 3
<211> LENGTH: 11
<212> TYPE: PRT
<213> ORGANISM: Human immunodeficiency virus

<400> SEQUENCE: 3

Tyr Gly Arg Lys Lys Arg Arg Gln Arg Arg
1               5                   10

<210> SEQ ID NO 4
<211> LENGTH: 7
<212> TYPE: PRT
<213> ORGANISM: Homo sapiens

<400> SEQUENCE: 4

Trp Lys Leu Gly Phe Phe Lys
1               5

<210> SEQ ID NO 5
<211> LENGTH: 18
<212> TYPE: PRT
<213> ORGANISM: Artificial
<220> FEATURE:
<223> OTHER INFORMATION: fusion protein

<400> SEQUENCE: 5

Arg Pro Leu Lys Lys Lys Met Glu Lys Arg Pro Leu Lys Lys Lys Met
1               5                   10                  15

Glu Lys

<210> SEQ ID NO 6
<211> LENGTH: 27
<212> TYPE: PRT
<213> ORGANISM: Artificial
<220> FEATURE:
<223> OTHER INFORMATION: fusion protein

<400> SEQUENCE: 6

Lys Leu Gly Phe Phe Lys Arg Lys Tyr Glu Lys Met Thr Lys Asn Pro
1               5                   10                  15

Asp Glu Ile Asp Glu Thr Thr Glu Leu Ser Ser
            20                  25

<210> SEQ ID NO 7
<211> LENGTH: 21
<212> TYPE: DNA
<213> ORGANISM: Homo sapiens

<400> SEQUENCE: 7
ggcacaaagg aguuacauct t                                            21

<210> SEQ ID NO 8
<211> LENGTH: 21
```

```
<212> TYPE: DNA
<213> ORGANISM: Homo sapiens

<400> SEQUENCE: 8
ggaguuacau cuuaacacat t                                              21

<210> SEQ ID NO 9
<211> LENGTH: 6
<212> TYPE: PRT
<213> ORGANISM: Homo sapiens

<400> SEQUENCE: 9

Trp Lys Ile Gly Phe Phe
1               5
```

METHOD FOR ACTIVATING T CELL PROTEIN TYROSINE PHOSPHATASE FOR THERAPEUTIC APPLICATIONS

CROSS-REFERENCE TO RELATED APPLICATIONS

This application is a continuation-in-part of PCT/FI2005/000203, filed 2 May 2005, which is related to and claims priority under 35 U.S.C. §119(e) to U.S. provisional patent application Ser. No. 60/576,029, filed 2 Jun. 2004. Each application is incorporated herein by reference.

FIELD OF THE INVENTION

This invention relates to a method for activation of T cell protein tyrosine phosphatase (TCPTP) and a method for inhibiting tyrosine kinase signalling in an individual. Further, the invention concerns a method for preventing or treating a disease or disorder in an individual, wherein said disease or disorder is curable by inhibiting tyrosine kinase signalling. Still further, the invention concerns a method for preventing cancer, or preventing or inhibiting cancer growth, invasion or metastasis in an individual, based on activating T cell protein tyrosine phosphatase (TCPTP). The invention also concerns pharmaceutical compositions useful in the methods.

BACKGROUND OF THE INVENTION

The publications and other materials used herein to illuminate the background of the invention, and in particular, cases to provide additional details respecting the practice, are incorporated herein by reference and set forth in the Bibliography.

Integrin-mediated cell adhesion regulates a multitude of cellular responses including proliferation, survival and cross-talk between different cellular signalling pathways[1]. Thus far, integrins have been mainly shown to convey permissive signals enabling anchorage-dependent receptor tyrosine kinase signalling[2,3]. In response to cell adhesion, integrins activate certain cytoplasmic signalling pathways directly and modulate signalling by growth factor receptors. indirectly. The cytoplasmic domains of integrins are essential in mediating these functions[4-7]. However, they lack intrinsic catalytic activity and require interactions with cytoplasmic proteins for signalling. Although collagen is a very abundant protein in the human body, relatively little is known about signalling of the four collagen binding integrins, α1β1, α2β1, α10β1 and α11β1. Integrin α1β1 is a receptor for collagens and laminins. Its a-subunit has been shown to associate with caveolin-1 and thus recruit signalling adaptor protein Shc[8]. This in turn leads to the activation of the mitogen-activated protein kinase pathway and increased survival and proliferation of fibroblasts on collagen[9]. In addition, the conserved region found in all integrin a-cytoplasmic tails has been shown function in focal adhesion assembly via the association with paxillin, talin and focal adhesion kinase[10]. However, thus far signalling pathways specifically activated by α1 integrin alone have remained unidentified.

SUMMARY OF THE INVENTION

A basis for the present invention is the discovery that the cytoplasmic tail of alpha-1-integrin selectively and directly interacts with a ubiquitously expressed protein tyrosine phosphatase TCPTP (T cell protein tyrosine phosphatase) and activates it upon cell adhesion to collagen. The activation results in reduced EGFR (epidermal growth factor receptor) phosphorylation upon EGF stimulation. The cytoplasmic tail of alpha-1-integrin functions as a negative regulator of EGFR signalling via the activation of a tumor suppressor protein, TCPTP. Introduction of the alpha-1 cytoplasmic domain peptide into cells induces phosphatase activation and inhibits EGF induced cell proliferation and anchorage-independent growth of malignant cells in vitro as well as in human fibrosarcoma zenografts in vivo. These data are the first demonstration of the regulation of TCPTP activity in vivo and represent a new molecular paradigm of integrin-mediated negative regulation of receptor tyrosine kinase signalling.

Thus, according to one aspect, this invention concerns an agent being either i) a peptide consisting of the amino acid sequence RPLKKKMEK (SEQ ID NO:1), or ii) a vector being capable of expressing said peptide in a mammalian cell, for use in therapy.

According to another aspect, the invention concerns a method for activation of T cell protein tyrosine phosphatase (TCPTP) in an individual by administering to said individual an effective amount of an agent, which is either i) a peptide consisting of the amino acid sequence RPLKKKMEK (SEQ ID NO:1), or ii) a vector being capable of expressing said peptide in a mammalian cell, or iii) a small molecule.

According to a third aspect, the invention concerns a method for inhibiting tyrosine kinase signalling in an individual, by administering to said individual an effective amount of an agent capable of activating T cell protein tyrosine phosphatase (TCPTP).

According to a fourth aspect, the invention concerns a method for preventing or treating a disease or disorder in an individual, said disease or disorder being curable by inhibiting tyrosine kinase signalling, by administering to said individual an effective amount of an agent capable of activating T cell protein tyrosine phosphatase (TCPTP).

According to a fifth aspect, the invention concerns a method for preventing cancer, or preventing or inhibiting cancer growth, invasion or metastasis in an individual, by administering to said individual an effective amount of an agent capable of activating T cell protein tyrosine phosphatase (TCPTP).

According to a sixth aspect, the invention concerns a pharmaceutical composition comprising a therapeutically effective amount of either a small molecule, able to activate TCPTP, or a peptide consisting of the amino acid sequence RPLKKKMEK (SEQ ID NO:1), and a pharmaceutically acceptable carrier.

According to a seventh aspect, the invention concerns a pharmaceutical composition comprising an expression vector encompassing a nucleic acid encoding a peptide consisting of the amino acid sequence RPLKKKMEK (SEQ ID NO:1), said vector being capable of expressing said peptide in a mammalian cell, and a pharmaceutically acceptable carrier.

Figure 1A:
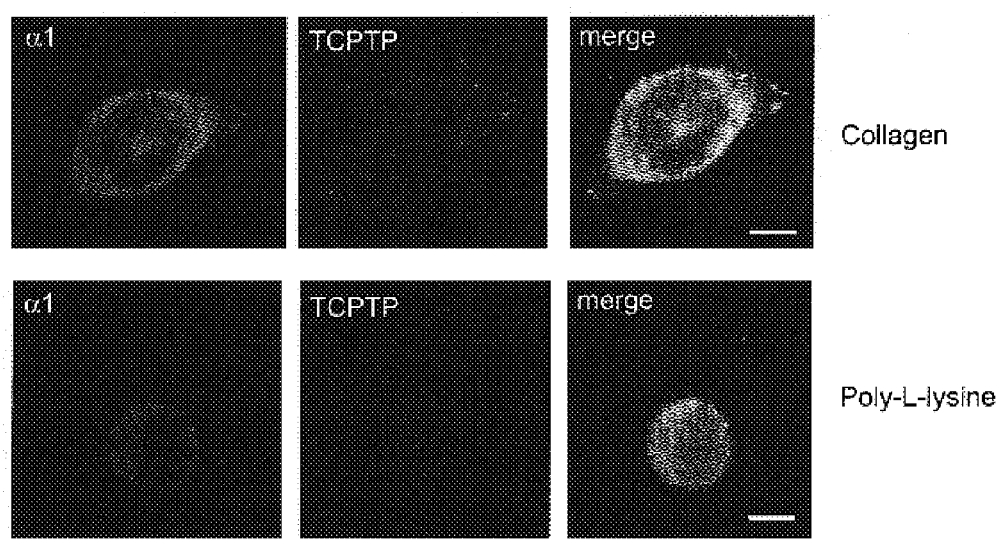
FIGS. 1A to 1F show that TCPTP associates with the cytoplasmic domain of integrin α1-chain. PC3 (FIG. 1A) and HeLa (FIG. 1B) cells were allowed to adhere to collagen, fibronectin or poly-L-lysine for 1 hour. Integrin α1 subunit and TCPTP were detected with two-color immunofluorescence stainings. Arrows point to representative areas of co-localization at the membrane. Pixel intensities for green and red (means±SEM, n=12) were assessed starting from the cell edge with the confocal microscope software; bar 5 µm. Serum-starved HeLa cells (FIG. 1C) were surface biotinylated and left on plastic, stimulated with 10% FBS for 30 min (FBS) or plated on collagen I (CI) or poly-L-lysine (PL) for 1 h. Immunoprecipitated (ip) integrins, TCPTP and controls (IgG) were detected in immunoblottings. HeLa cells (FIG. 1D) were treated as in FIG. 1C, lysates were immunoprecipitated (ip) and blotted for TCPTP or denatured and re-precipitated (re-ip) with an anti-α1 antibody and immunoblotted as indicated. HeLa cell lysate (FIG. 1E) was incubated with immobilized glutathione-S-transferase (GST) or with GST-integrin cytoplasmic domain fusion proteins. Bound proteins and lysate samples were probed for TCPTP. Ponceau S staining was used to control loading. Recombinant and purified TCPTP (1 µg) (FIG. 1F) was incubated with GST or GST-fusion proteins with or without α1 integrin cytoplasmic domain peptide (1 µg/ml). Bound proteins (and TCPTP loading control, total) were probed for TCPTP and GST.
Figure 1B:
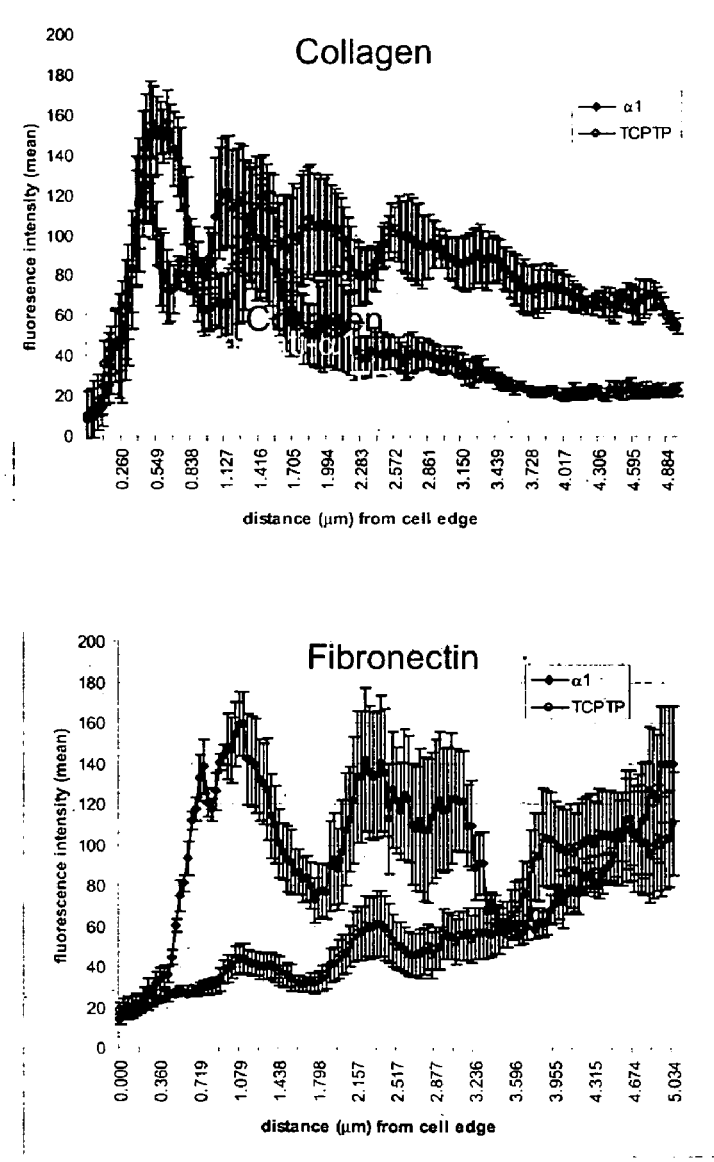
Figure 1C:
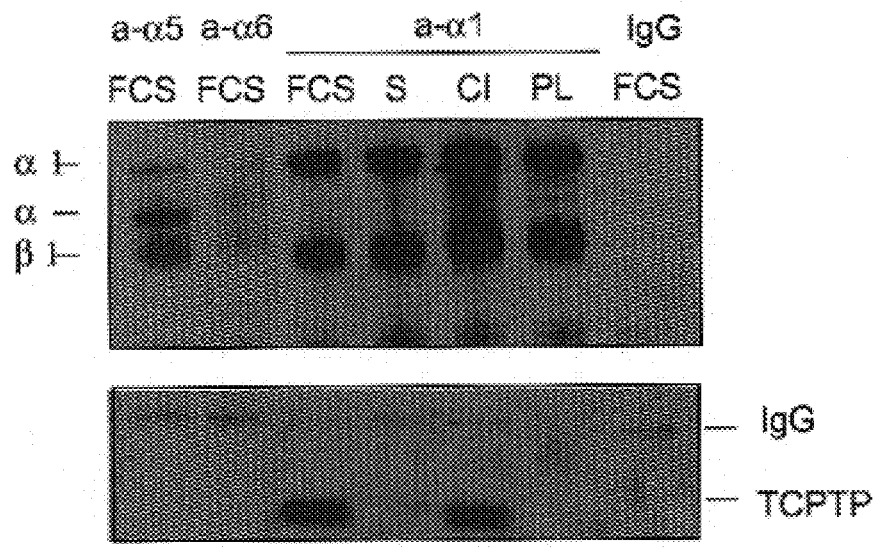
Figure 1D:
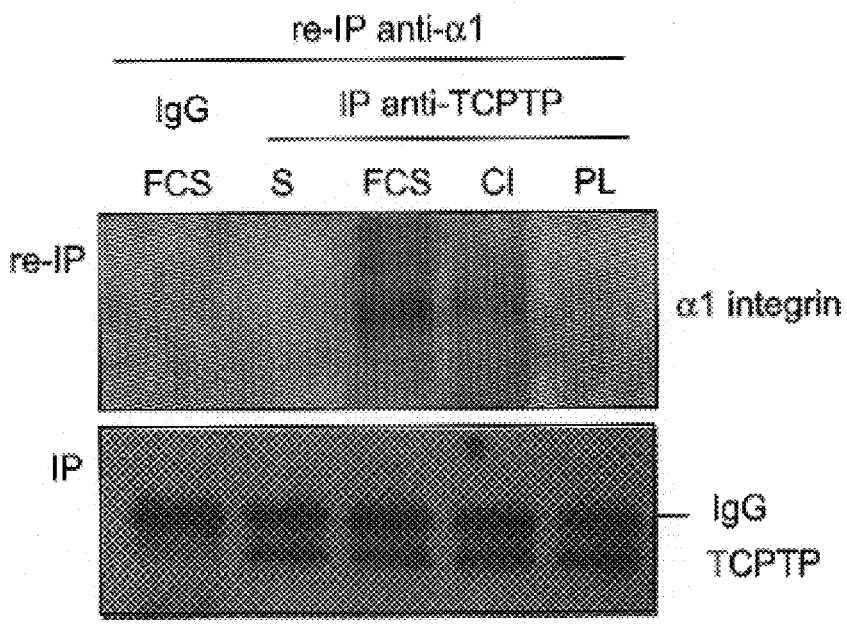
Figure 1E:
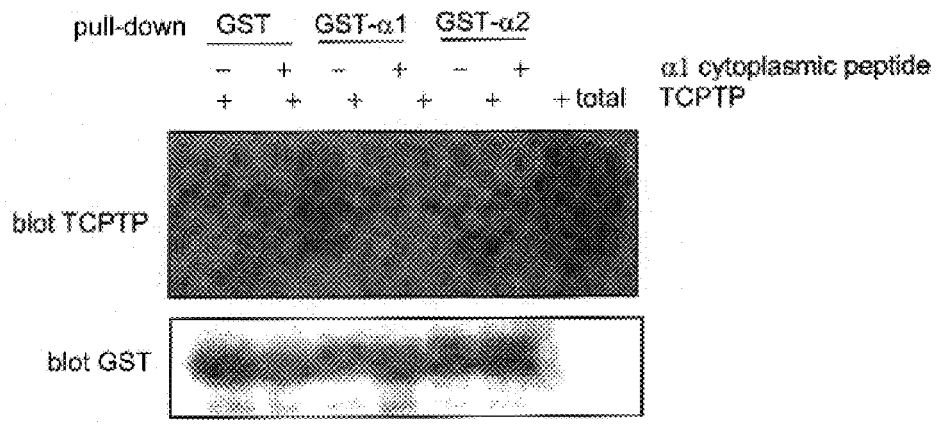
Figure 1F:
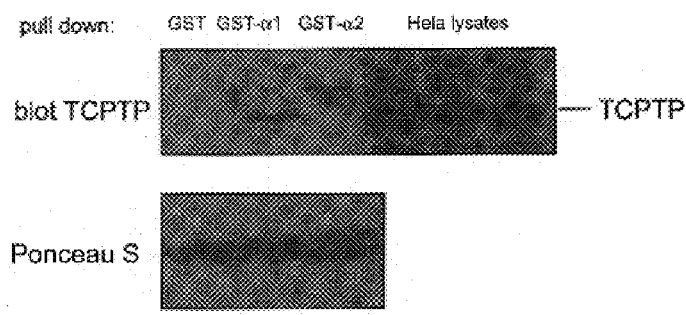
Figure 1G:
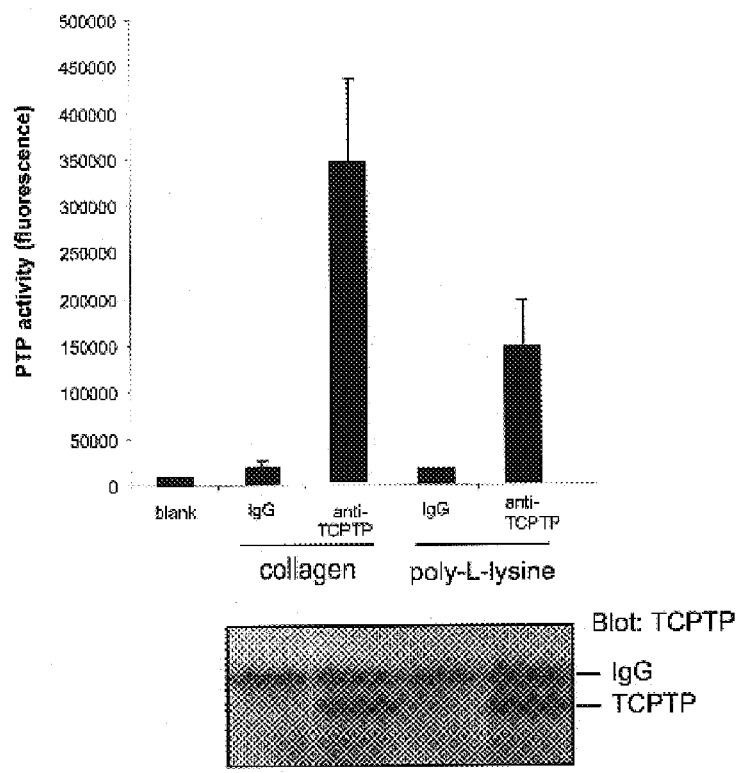
Figure 1H:
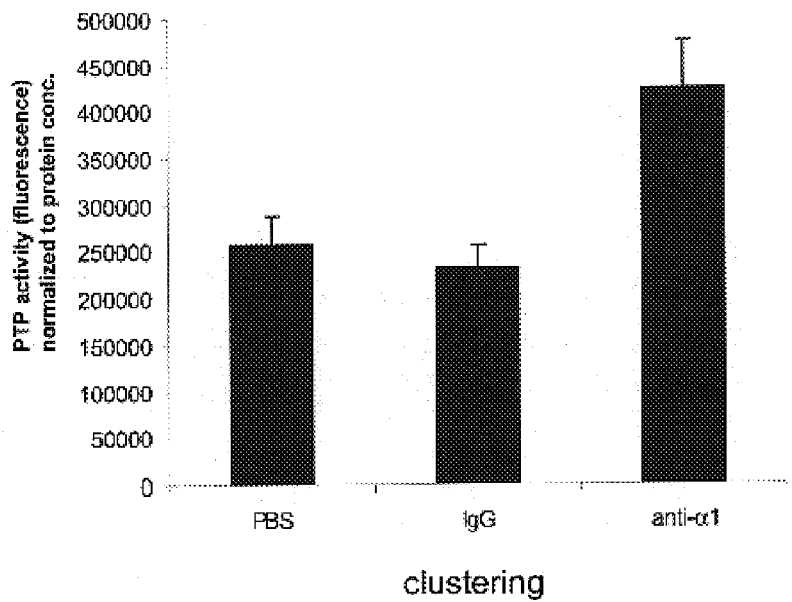

FIGS. 1G to 1H show adhesion to collagen and clustering of α1-integrin activate TCPTP. Serum-starved HeLa cells (FIG. 1G) were detached, plated on collagen or poly-L-lysine, subjected to immunoprecipitations (ip) and phosphatase activity (means±SD, n=3) was determined. Half of the samples were immunoblotted for TCPTP. Serum-starved HeLa cells (FIG. 1H) were incubated with PBS, control IgG or anti-α1 mAb and clustering was induced with an anti-mouse secondary antibody for 30 min. Equal amounts of protein from lysates were assayed for phosphatase activity (means±SD, n=3) in triplicates.

Figure 2A:
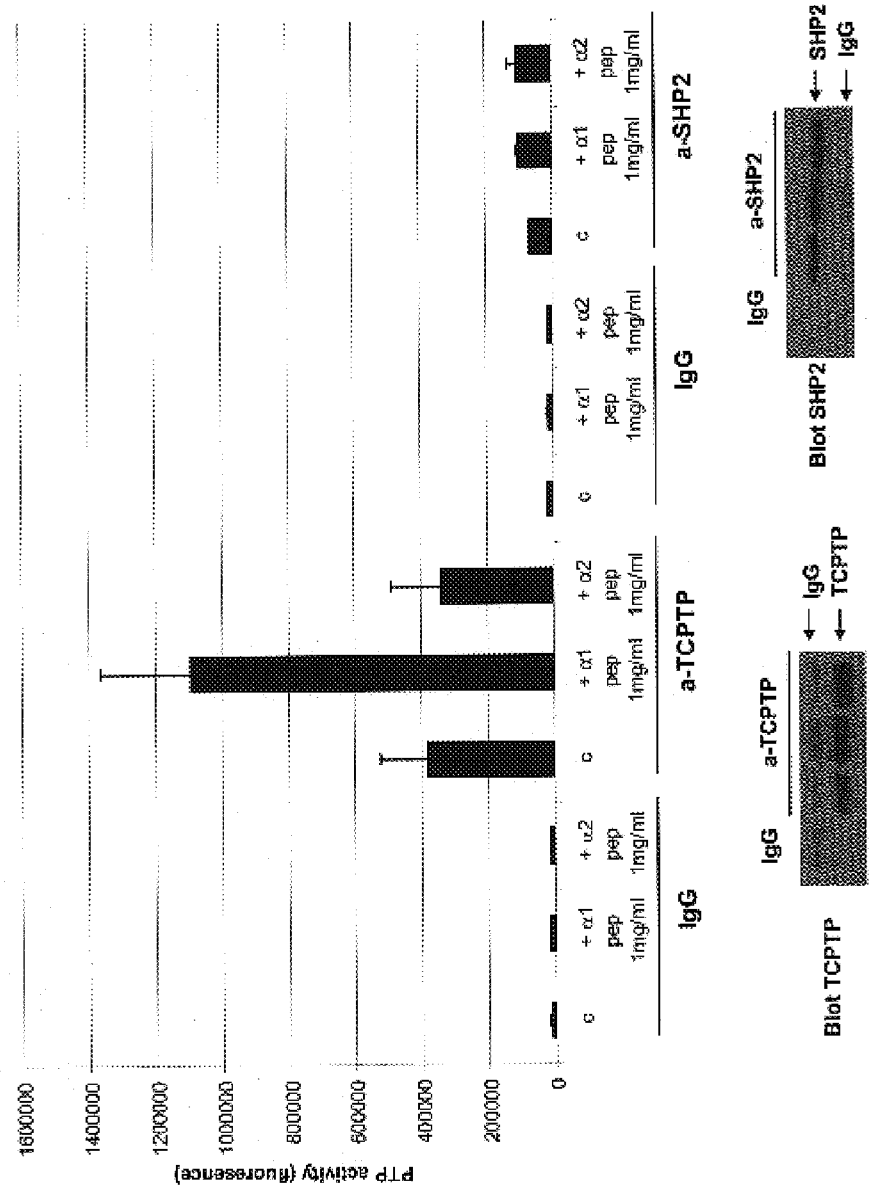
Figure 2B:
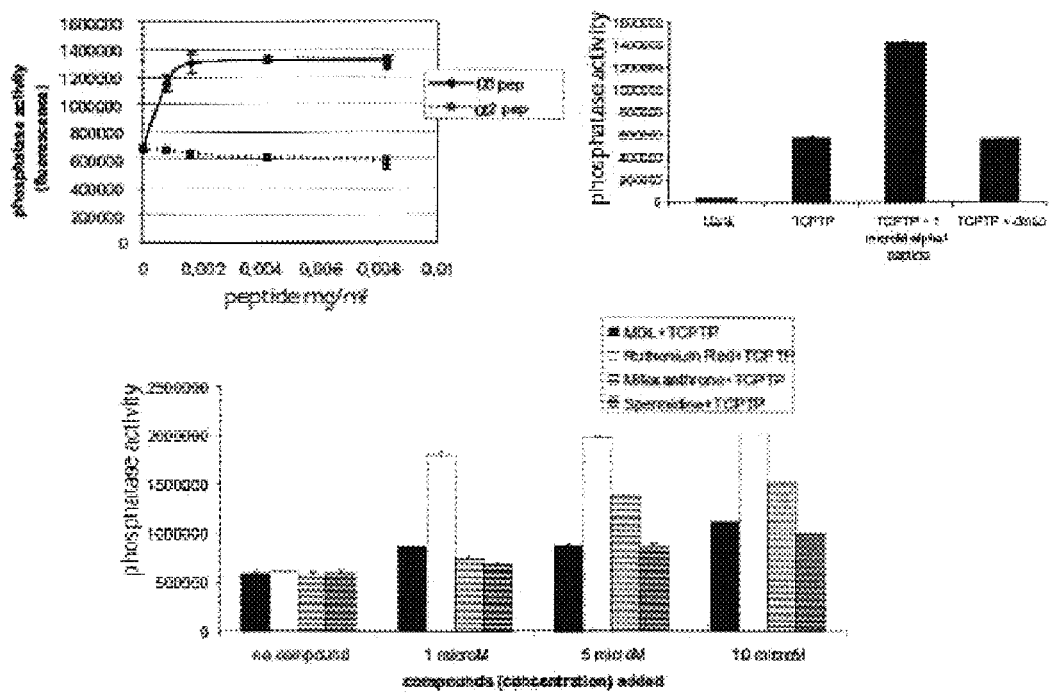
Figure 2C:
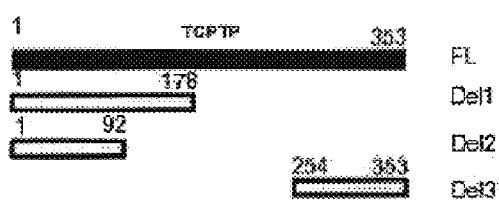

FIGS. 2A to 2D show that the integrin α1 cytoplasmic tail activates TCPTP. HeLa lysates (FIG. 2A) were immunoprecipitated (ip) with control (IgG), anti-TCPTP and anti-SHP-2 antibodies. The phosphatase activity (means±SD, n=3) was analyzed using diFMUP as the substrate after treatments with vehicle (c), and synthetic α1 (α1pep) and α2 (α2pep) cytoplasmic tail peptides. Half of the immunoprecipitates were resolved on SDS-PAGE and probed for TCPTP or SHP-2. Recombinant, purified TCPTP (0.15 µg/ml) (FIG. 2B) was incubated with different peptide concentrations and analyzed for the phosphatase activity (means±SD, n=3). Recombinant, purified TCPTP (0.1 µg/ml) (FIG. 2B) was incubated with 1 µM synthetic α1 (α1pep) cytoplasmic tail peptide as a positive control or different concentrations of commercially available small molecules and analyzed for the phosphatase activity. FIG. 2C shows schematic diagrams of the TCPTP deletion mutants. In competition assay (FIG. 2D), TCPTP deletion mutants fused to GST or GST alone were incubated with peptides as indicated before full length TCPTP was added and phosphatase activity (means±SD, n=3) measured.

Figure 2D:
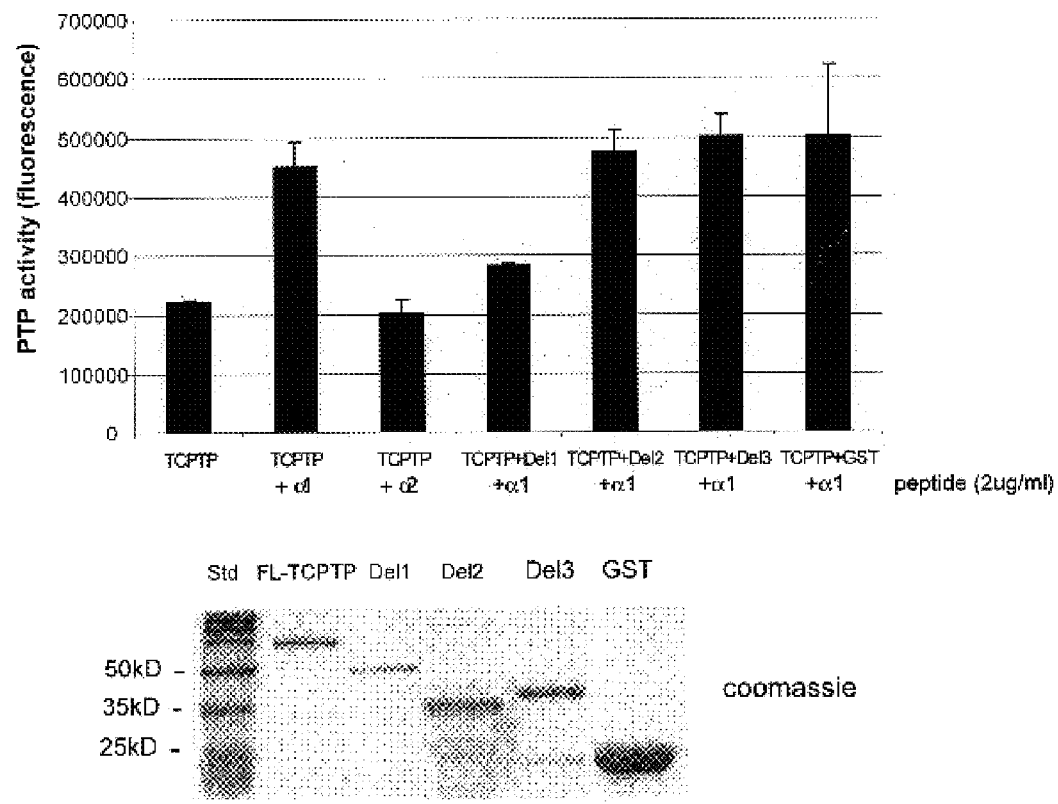
Figure 2E:
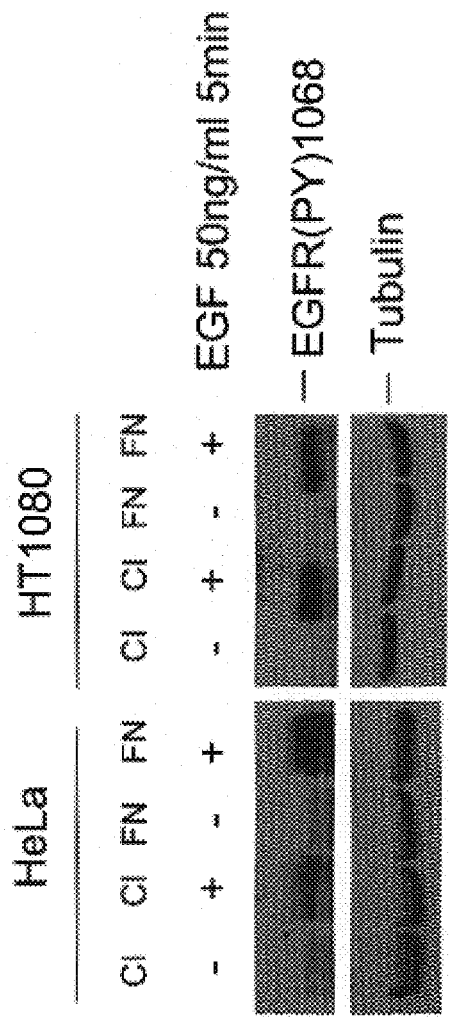
Figure 2F:
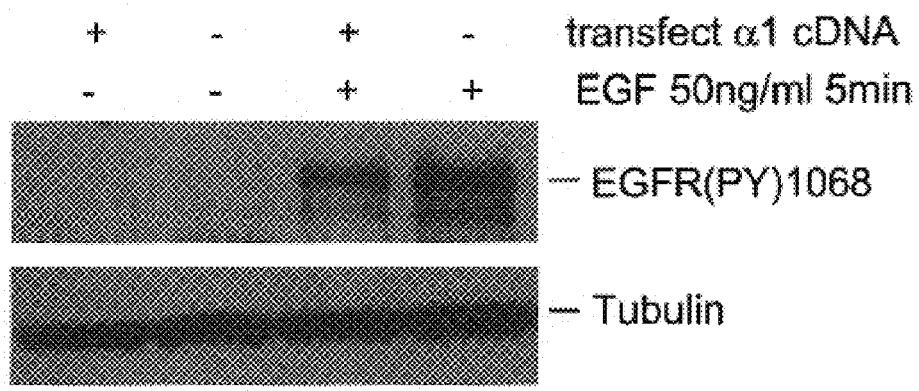
Figure 2G:
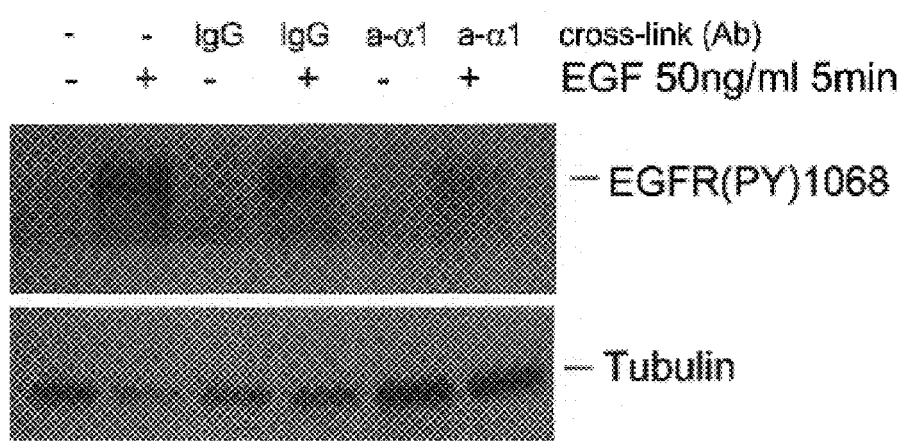

FIGS. 2E to 2G show that integrin $\alpha_1\beta_1$ is required for collagen induced attenuation of EGFR signalling. HeLa and HT1080 cells were analyzed (FIG. 2E) for surface expression of the integrins using FACS and MFI values are shown. Serum-starved HeLa and HT1080 cells were plated on collagen I (CI) or fibronectin (FN) and treated with EGF. EGFR phosphorylation was studied using phospho-specific antibody. Tubulin was used as a loading control. HT1080 cells transiently transfected (FIG. 2F) with α1-cDNA or mock-transfected were serum-starved, plated on collagen I (CI) and treated with EGF. EGFR phosphorylation was analyzed as in FIG. 2E. Serum-starved HeLa cells (FIG. 2G) were treated as in FIG. 1H to cross-link α1 receptors and EGFR phosphorylation was studied by immunoblotting.

FIGS. 3A to 3F show that integrin α1β1 ligation attenuates EGFR phosphorylation via activation of TCPTP. Serum-starved HeLa cells (FIGS. 3A, 3B, 3C) maintained on plastic or plated on collagen I (CI) or fibronectin were treated with EGF and EGFR phosphorylation was studied using phospho-specific antibodies. Densitometric analyses of three (A, C) experiments (means±SD) are shown. Tubulin or EGFR were used as loading controls. HeLa cells (FIG. 3D) transfected with two siRNAs specific for TCPTP (or scramble control) were plated on collagen and treated with EGF. Extracts were immunoblotted for the indicated proteins. A representative of three experiments with similar results is shown. Fibroblasts from α1−/−mice or their wild-type (FIG. 3E) littermates were plated on collagen and immunostained for integrin α1 and TCPTP. Pixel intensity for green and red (means±SEM, n=12) were analyzed starting from the cell edge with confocal microscope software; bar 5 µm. Serum-starved fibroblasts (FIG. 3F) from α1−/−and +/+animals ( ) were plated on collagen or fibronectin, treated with EGF, and immunoblotted. Values are densitometric quantitations normalized to tubulin.

Figures 3A, 3B:
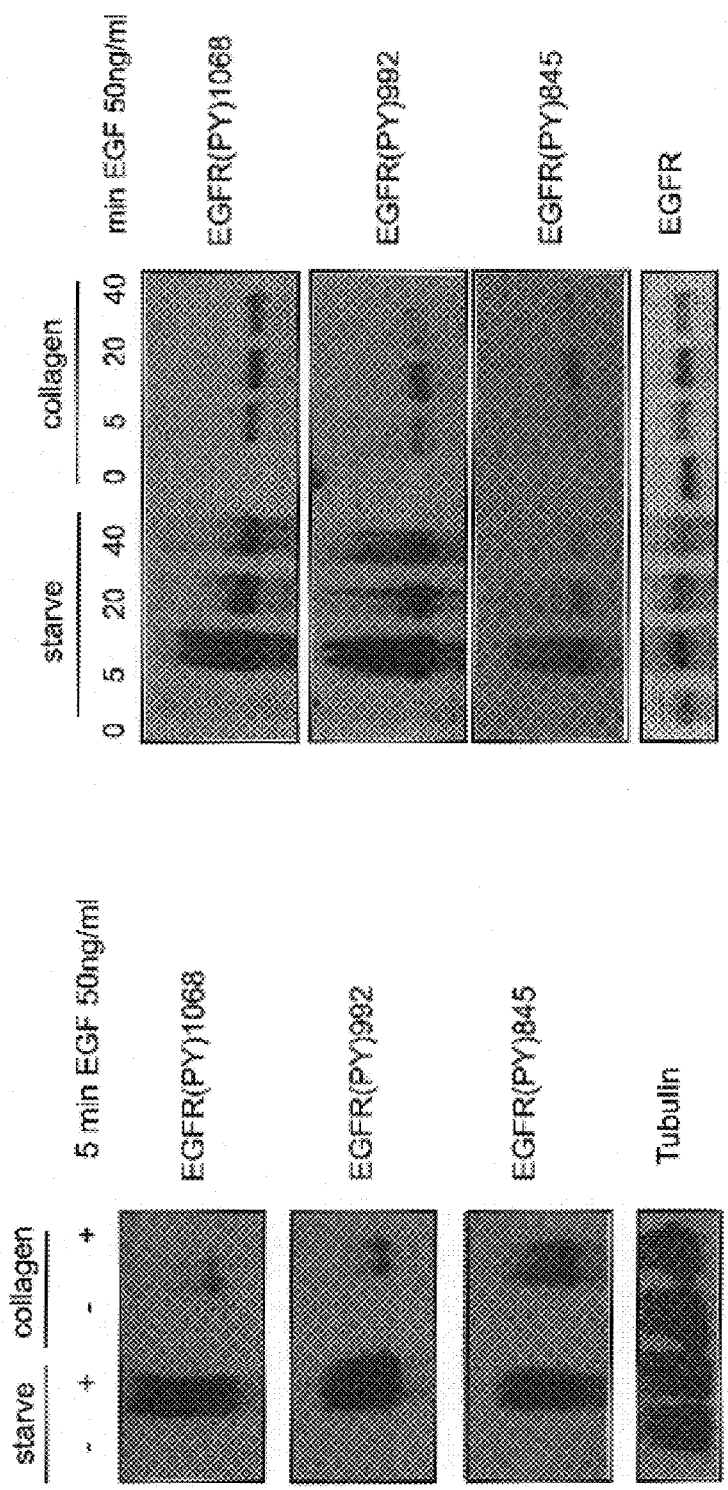
Figure 3C:
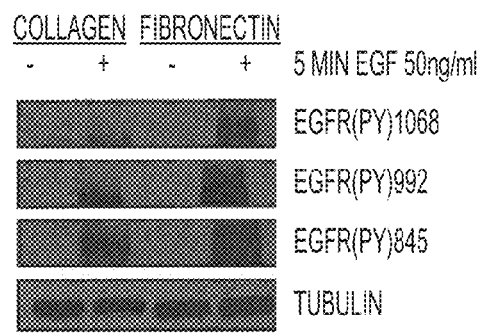
Figure 3C:
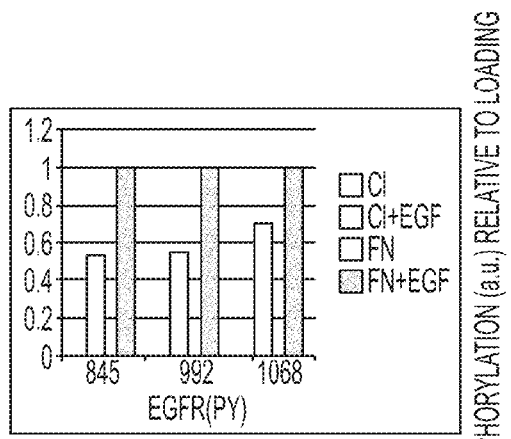
Figure 3D:
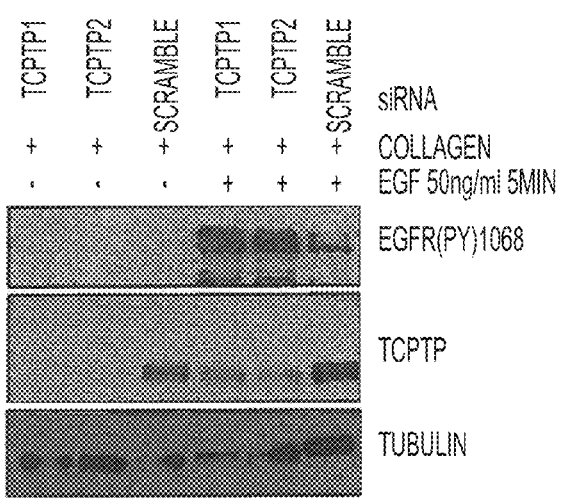
Figure 3E:
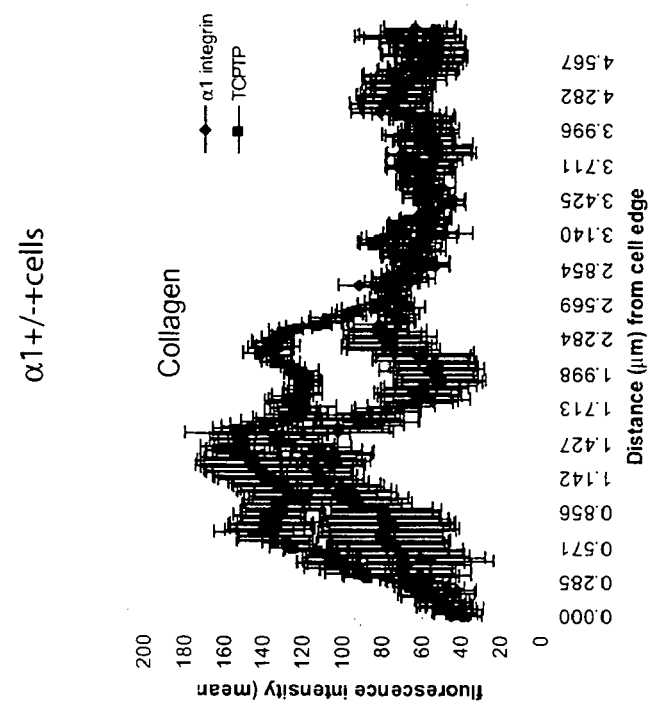
Figure 3E:
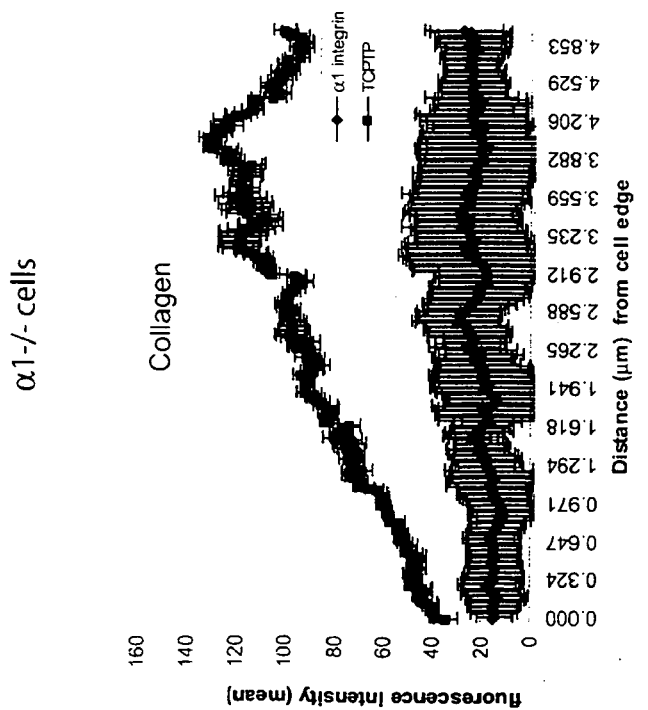
Figure 3F:
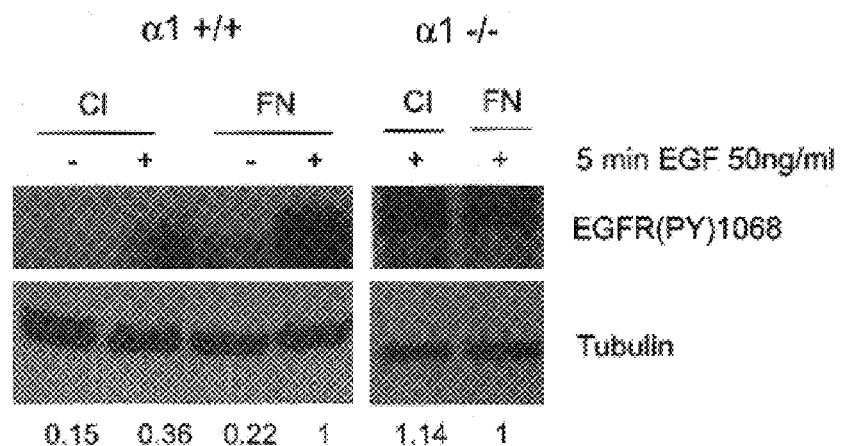
Figure 3G:
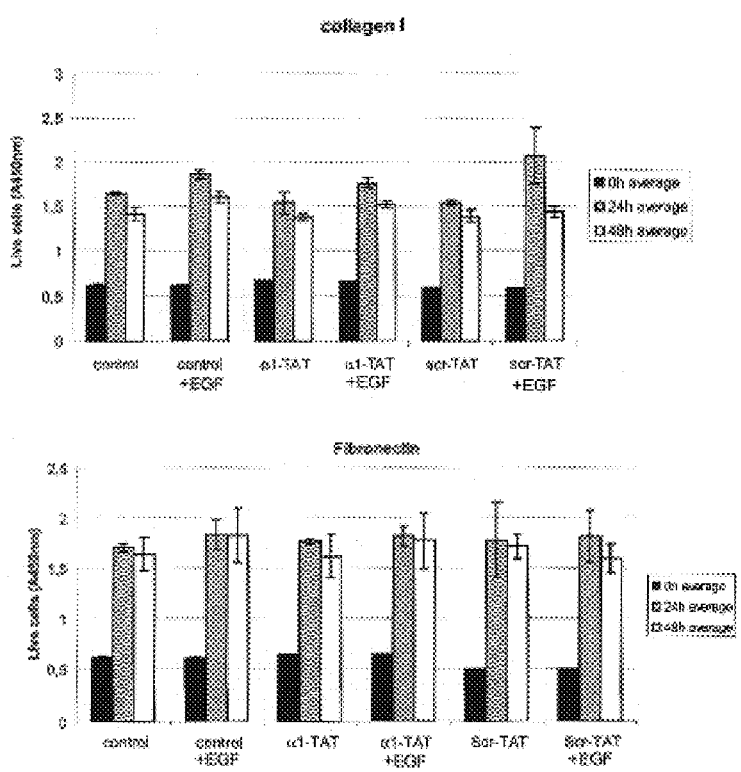

FIG. 3G shows that integrin α1 cytoplasmic peptide does not affect EGF-independent proliferation of matrix-adherent cells. HeLa cells were cultured in collagen or fibronectin coated wells in 5% serum in the presence or absence of 200 nM TAT-peptides and 50 ng/ml EGF and the numbers of live cells (means±SD, n=3) at various time points was analyzed.

Figure 4A:
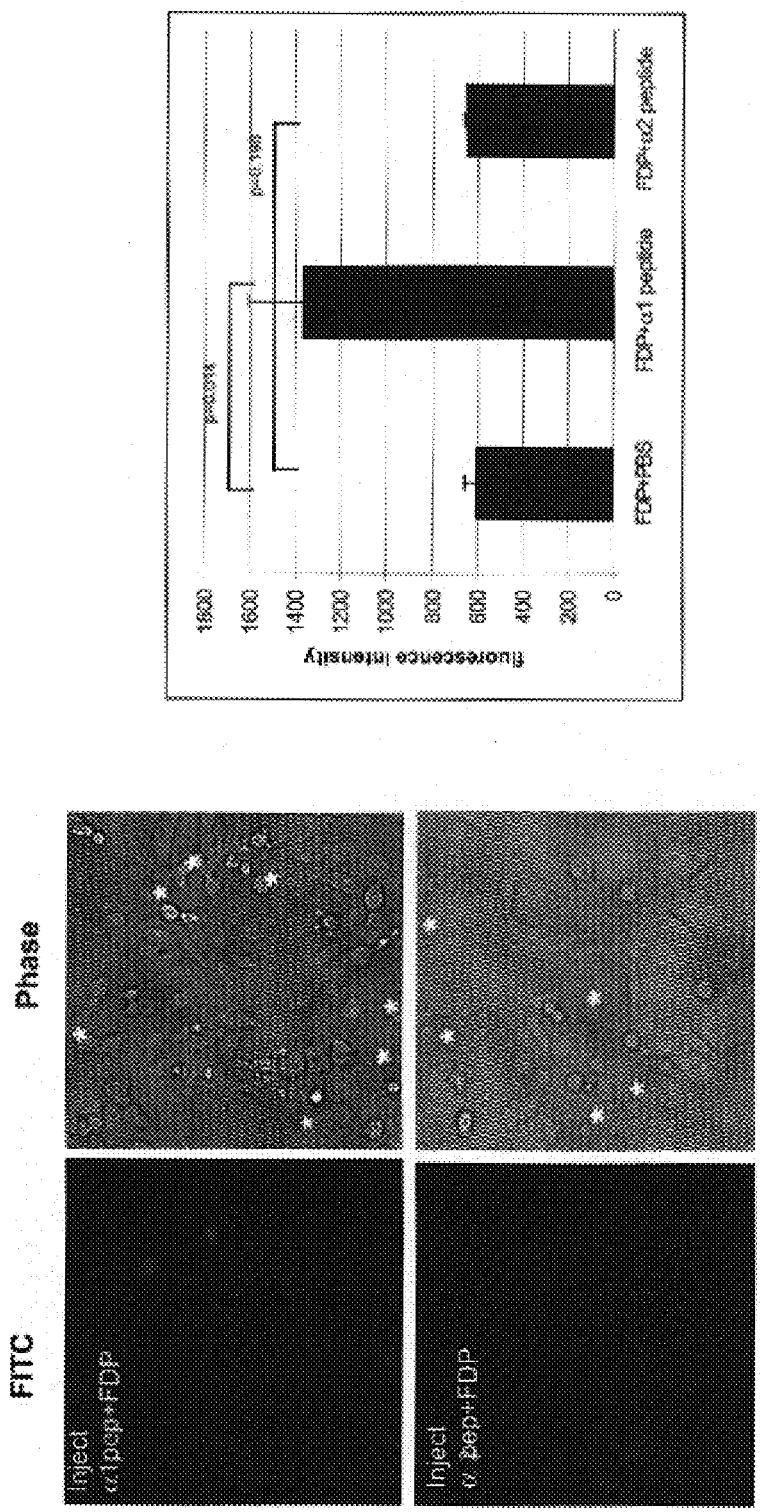
Figure 4B:
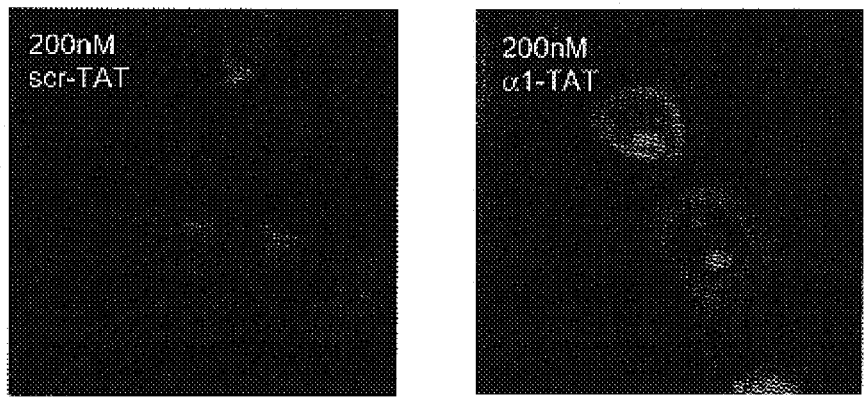
Figure 4B:
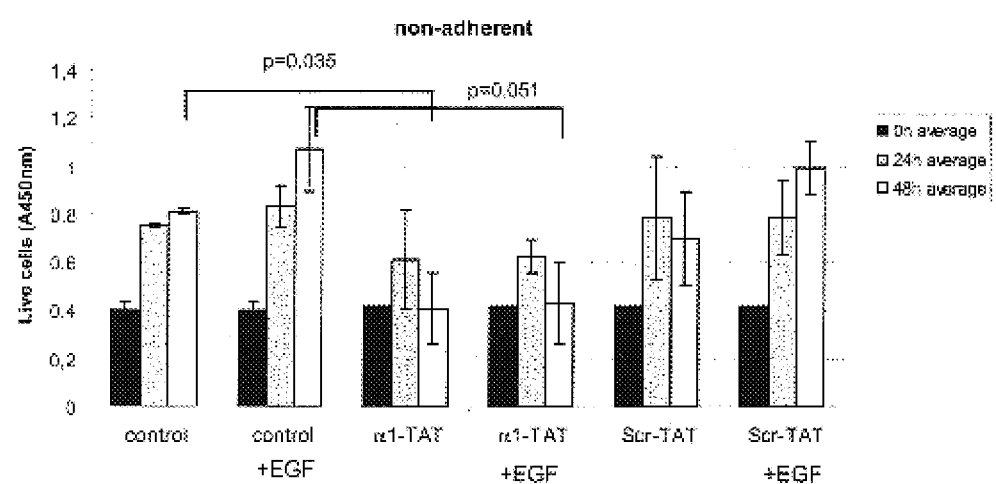
Figure 4C:
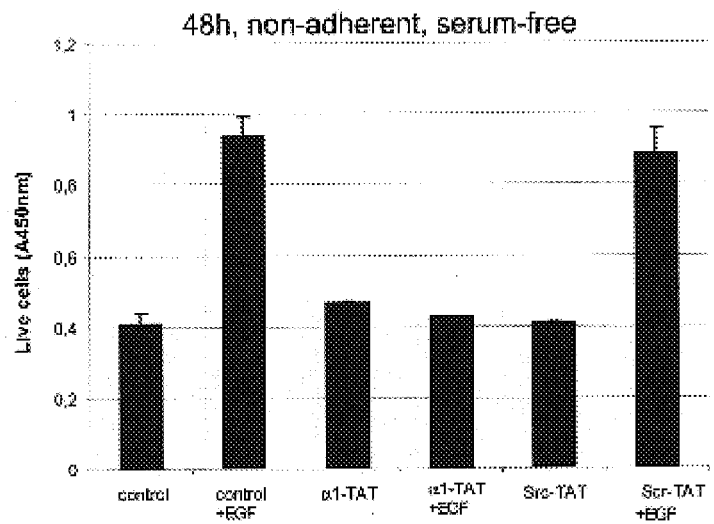
Figure 4D:
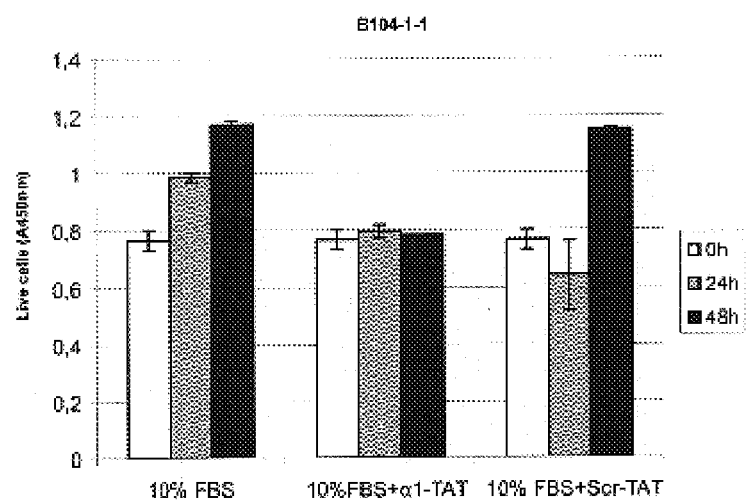
Figure 4E:
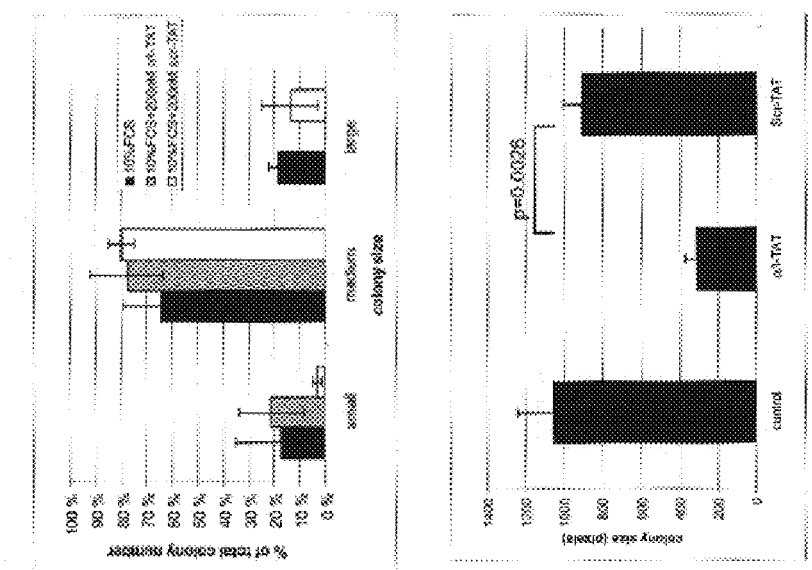
Figure 4E:
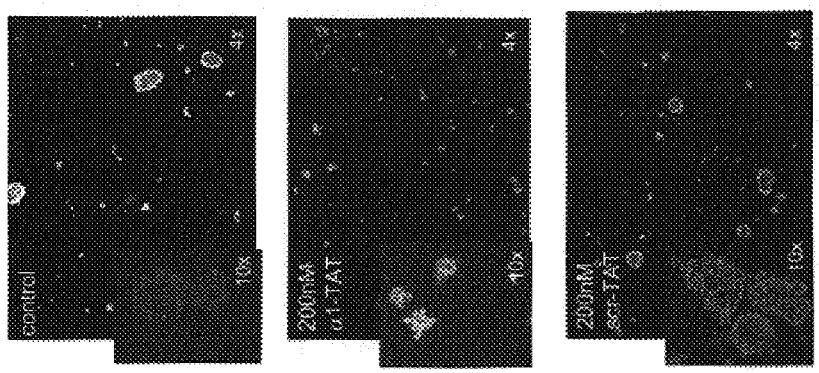

FIGS. 4A to 4E show that α1 cytoplasmic tail peptide induces phosphatase activity in vivo and inhibits anchorage-independent and EGF-induced cell growth. HeLa cells (FIG. 4A) were microinjected (asterixes) with fluorescein diphosphate (FDP), that becomes fluorescent upon dephosphorylation, and cytoplasmic integrin peptides. Fluorescence intensity was monitored for 30 min (representative images at 30 min are shown) and mean intensity in individual cells (means±SEM, n=12) was measured. FIG. 4B shows that FITC-labeled TAT-α1 cytoplasmic tail fusion peptide (α1-TAT) and TAT-scramble control fusion peptide (Scr-TAT) enter into HeLa cells. Their effect on the number of (FIG. 4B) live non-adherent HeLa cells in 5% serum, HeLa cells (FIG. 4C) in serum-free medium and (FIG. 4D) tumorigenic B 104-1-1 fibroblasts in serum and in the presence or absence of 200 nM TAT-peptides and 50 ng/ml EGF was measured (means±SD, n=3). HeLa cells were grown for 9-days in agarose with or without the TAT-peptides (FIG. 4E). Representative phase contrast images taken double-blindly and analyzes of colony sizes are shown.

Figure 5A:
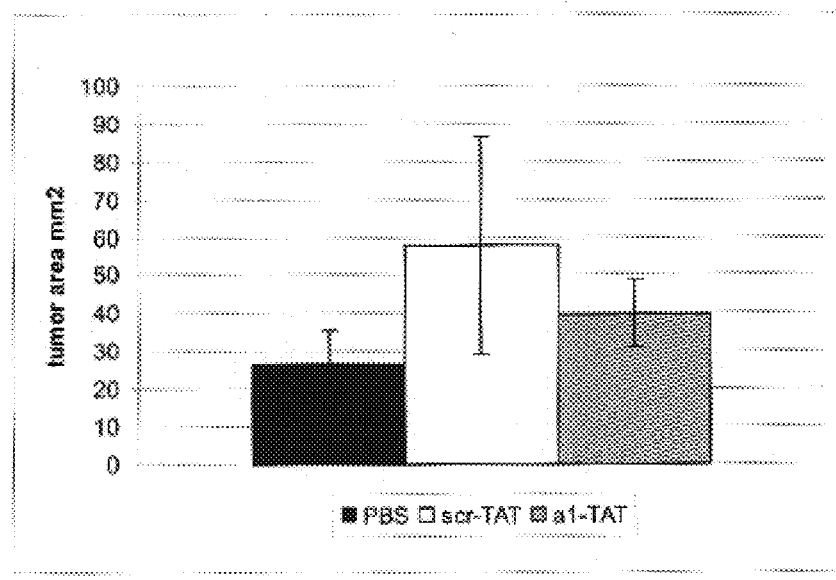
Figure 5B:
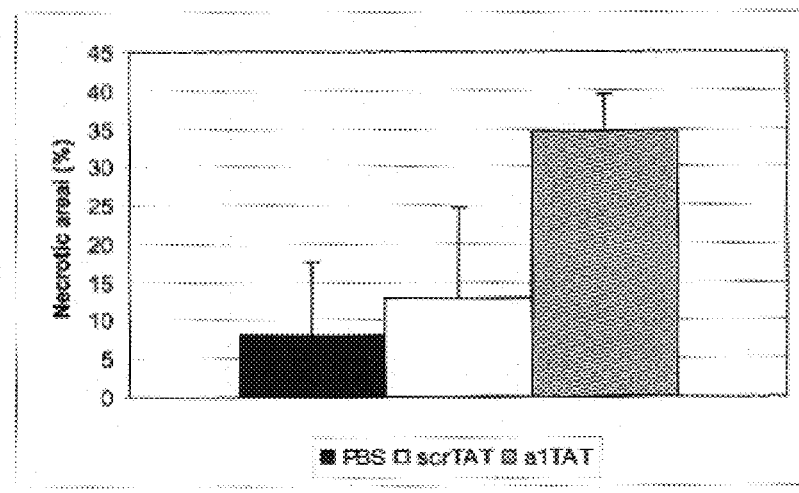

FIGS. 5A and 5B show that α1 cytoplasmic tail peptide reduces tumor growth and induces necrosis in vivo. HT1080 human fibrosarcoma cells were injected into the flanks of nude mice and treated as indicated in experimental section. Subdermal tumors were removed after 4 weeks. The size (area) of the tumors was measured and are shown in FIG. 5A (means±SEM, n=12). Whole-tumors cross sections were stained with Masson-trichorome staining and areas of necrosis relative to the whole tumor area were scored double-blindly (FIG. 5B, means±SEM, n=12). Analyzes of necrotic areas are shown.

DETAILED DESCRIPTION OF THE INVENTION

Definitions

The term "treatment" or "treating" shall be understood to include complete curing of a disease or disorder, as well as amelioration or alleviation of said disease or disorder.

The term "prevention" shall be understood to include complete prevention, prophylaxis, as well as lowering the individual's risk of falling ill with said disease or disorder.

The term "individual" refers to a human or animal subject.

The term "effective amount" is meant to include any amount of an agent according to the present invention that is sufficient to bring about a desired therapeutical result, especially upon administration to an animal or human subject.

The term "peptide" shall be understood to include peptides of L-amino acids, D-amino acids or both.

Preferable Embodiments

The agent to be used for activation of TCPTP can either be a small molecule able to activate TCPTP, or a peptide consisting of the amino acid sequence RPLKKKMEK (SEQ ID NO:1). This sequence is specific for the cytoplasmic tail of alpha-1-integrin. The peptide can, according to one embodiment, be exactly the amino acid sequence RPLKKKMEK (SEQ ID NO:1), which could be administered to the cell by microinjection, for example.

Alternatively, the peptide can be a longer chain encompassing the amino acid sequence RPLKKKMEK (SEQ ID NO:1). According to a particularly preferable embodiment, the peptide (the chain RPLKKKMEK (SEQ ID NO:1) or a longer chain encompassing the same) can be part of a cell membrane permeable fusion protein. As an example of such a fusion protein can be mentioned a fusion protein comprising a protein transduction domain of HIV transcriptional transactivator (TAT) protein and the amino acid sequence RPLKKKMEK (SEQ ID NO:1). As a specific example of such fusion proteins can be mentioned YGRKKRRQRRRWKLGFFKRPLKKKMEK (SEQ ID NO:2). The sequence YGRKKRRQRRR (SEQ ID NO:3) is derived from TAT and the sequence WKLGFFK (SEQ ID NO:4) is derived from the integrin (typical for any alpha-integrin).

According to a further alternative, the agent to be administered can be a vector, comprising a nucleic acid being capable of expressing the desired peptide in a mammalian cell. The nucleic acid can be inserted in a DNA sequence, an RNA sequence or in a viral vector. Such a viral vector is typically based on an adenovirus, an alphavirus, adeno-associated virus, a retrovirus or a herpes virus. For expression of peptides in cells, see for example M Parsons et al., Molecular and Cellular Biology, August 2002, p. 5897-5911.

Activation of TCPTP according to this invention can thus be used to prevent or treat disorders or diseases that are directly or indirectly influenced by said activation.

As examples of diseases or disorders at least partly indirectly influenced can be mentioned any disease or disorder, the curability of which would benefit from inhibiting tyrosine kinase signalling. As specific, non-limiting examples of such targets can be mentioned an epidermal growth factor receptor (EGFR), an insulin receptor and a Janus kinase. Inhibition of EGFR will be useful in preventing cancers, preventing or inhibiting cancer growth, invasion or metastasis. However, these effects might also partly be due to other mechanisms caused by the activation of TCPTP.

On the other hand, the inhibition of EGFR may also be useful in prevention or treatment of other, non-cancer diseases or disorders.

Inhibition of the insulin receptor and Janus kinase may be useful in the treatment or prevention of disorders associated with overactive insulin initiated signalling leading to abnormal energy metabolism regulated by the insulin receptor and disorders associated with unwanted inflammatory signalling by interferons which leads to abnormal activation of Janus kinase that associates with the interferon receptor.

The peptide comprising the sequence RPLKKKMEK (SEQ ID NO:1) is preferably brought in a form which allows permeation through the cell membrane. Such a peptide can be admixed with any carrier that is suitable for parenteral administration of the composition. For example, the peptide can be complexed with a lipid, packed in a liposome, incorporated in a cyclodextrin or other complexing agent, a bioresorbable polymer or other suitable carrier for controlled release administration, or encompassed in a nanoparticle or hydrogel.

Alternatively, an expression vector encompassing a nucleic acid encoding a peptide comprising the amino acid sequence RPLKKKMEK (SEQ ID NO:1) can be administered to the individual. The nucleic acid can encode the exact sequence RPLKKKMEK (SEQ ID NO:1) or a longer peptide comprising this sequence. The vector can, for example, be complexed with a lipid, packed in a liposome, incorporated in a cyclodextrin or other complexing agent, a bioresorbable polymer or other suitable carrier for controlled release administration, or encompassed in a nanoparticle or hydrogel.

The therapeutically effective amount of the peptide or expression vector to be given to a patient in need of such treatment may depend upon a number of factors including, for example, the age and weight of the patient, the precise condition requiring treatment and its severity, and the route of administration. The precise amount will ultimately be at the discretion of the attending physician. Thus, practice of the present invention may involve any dose, combination with other therapeutically effective drugs, pharmaceutical formulation or delivery system for parenteral administration. The peptide or expression vector can be administered systemically or locally. As suitable routes of administration can be mentioned intravenous, intramuscular, subcutaneous injection, inhalation, topical, ocular, sublingual, nasal, rectal, intraperitoneal delivery and iontophoresis or other transdermal delivery systems.

The invention will be illuminated by the following non-restrictive Experimental Section.

EXPERIMENTAL SECTION

Methods
Yeast-Two-Hybrid System

α1-integrin cytoplasmic domain was fused to GAL4 DNA-BD in the pGBKT7 vector (Clontech) and used as a bait to screen mouse 17-day embryo Matchmaker cDNA library (BD Clontech) Screening of the library was done according to manufacturer's protocol. One of the independent clones isolated that interacted with GAL4-DBD-α1cyt, but not with unrelated baits encodes the T-cell protein tyrosine phosphatase.

Small Molecule Compounds

The small molecule compounds described here to be able to activate TCPTP are all commercially available from Sigma. The compounds are Ruthenium Red, Spermidine, Mitoxantrone and MDL-26,630 trihydrochloride. All compounds were solubilised in DMSO at a concentration of 10 mM.

Protein-Protein Interaction Assays

α1cyt and a2cyt were subcloned into pGEX4T1 (Amersham Biosciences). Full length TCPTP (45 kD) and its deletion mutants were PCR-amplified from pCG-TC45 plasmid[11] and cloned into pGEX-6P-1. GST-fusion proteins were expressed in *E. coli* (BL21 pLysS) and purified using manufacturer's instructions (Amersham Biosciences). Fusion proteins were either used immobilized to Glutathione-sepharose, eluted with 25 mM glutathione or GST was cleaved using precision protease according to manufacturers instructions (Amersham Biosciences). For pull-down assays, Hela cells were lysed to lysis buffer (1% octylglycoside, 50 mM Tris-HCl pH 7.5, 150 mM NaCl, 1 mM MgCl2, complete protease inhibitor (Roche)), clarified with centrifugation 10 min 13000 rpm+4 C, precleared with glutathione-sepharose and incubated with immobilized GST-fusion proteins and washed 3 times with 1 ml on the same buffer. Bound proteins were resolved on SDS-PAGE and detected with western blot. Alternatively, purified full-length TCPTP was incubated in the lysis buffer with GST-fusion proteins as indicated in the presence or absence of synthetic integrin α1 cytoplasmic tail peptide (RPLKKKMEKRPLKKKMEK, (SEQ ID NO:5) Genemed Synthesis).

Immunoprecipitations, Western Blotting and Phosphatase Assays

Serum starved Hela cells were either left untreated on plastic, stimulated with 10% FBS for 30 min or detached and replated on collagen type I or poly-L-lysine (10 μg/ml, Sigma) coated tissue-culture plates for 1 h. When indicated cells were surface biotinylated as described[12]. Cells were either lysed in Laemmli sample buffer and fractionated on SDS-PAGE for western blotting or lysed in lysis buffer and equal amounts of protein from each sample were precleared with protein G-Sepharose and subjected to immunoprecipitation. Antibodies (anti-TCPTP, Oncogene; anti-α1, anti-α5, anti-α6, all from Chemicon; anti-SHP-2, Santa Cruz) were incubated with protein G-Sepharose and immunoprecipitation was performed at 4° C. for 2 h. The immunoprecipitates were washed three times with cell lysis buffer. For co-precipitation assays, proteins were resolved on SDS-PAGE followed with western blotting or detection of biotin with Vectastain reagent (Vector). For phosphatase assays, immunoprecipitates were resuspended in phosphatase reaction buffer (25 mM Hepes pH 7.4, 50 mM NaCl, 1 mM DTT) and ⅓ of the reaction was subjected to western blotting and the remaining beads were assayed for phosphatase activity in triplicate using diFMUP (Molecular Probes) as a substrate and in the presence of serine/threonine phosphatase inhibitor cocktail (Sigma) according to manufacturers instructions. When indicate synthetic peptides were preincubated with the immunoprecipitates for 15 min prior to phosphatase assay reaction (α2 peptide KLGFFKRKYEKMTKNPDEIDET-TELSS (SEQ ID NO:6), a kind gift from Dr Heino). For phosphatase assays with purified protein, full length TCPTP was incubated in phosphatase reaction buffer in the presence or absence of TCPTP deletion mutant proteins and synthetic integrin cytoplasmic tail peptides as indicated. For phosphatase assays with the small molecules the compounds or peptide were preincubated with 0.2 μg/ml TCPTP in reaction buffer for 10 minutes RT before the addition of diFMUP (Molecular Probes) as a substrate. The phosphatase reaction was allowed to proceed for 10 minutes in RT and stopped with urea followed with measurement of umbelliferone fluorescence according to manufacturers instructions (Molecular Probes). Western blotting was performed with commercial antibodies raised against EGFR, EGFR(PY)845, 992 or 1068 (Cell Signalling Technologies), TCPTP (Oncogene) or tubulin (Santa Cruz Biotechnology). Specific binding of antibodies was detected with peroxidase-conjugated secondary antibodies and visualized by enhanced chemiluminescence detection.

Transfections

HT1080 cells were transiently transfected with α1cDNA in pcDNA3.1/zeo vector (a kind gift from Dr Pozzi, Vanderbilt University) using Fugene 6 (Roche) reagent as described previously[13]. Two different annealed siRNAs targeting TCPTP (ggcacaaaggaguuacauctt (SEQ ID NO:7), ggaguua-caucuuaacacatt (SEQ ID NO:8); Ambion) or scramble control siRNA were transfected to Hela cells using Oligo-fectamine (Invitrogen) according to manufacturers protocol. 24 h post transfection cells were serum-starved for 24 h and treated as indicated before lysis and western blot analysis.

Immunofluorescence

Cells were plated on acid-washed glass coverslips coated with collagen type I, fibronectin or poly-L-lysine (10 μg/ml) and allowed to adhere for 1 h. Cells were washed in PBS and fixed with 4% paraformaldehyde for 10 min. For antibody staining, cells were permeabilized in PBS/0.1% Triton X-100 and washed with PBS/1% (w/v) BSA for blocking. Cells were stained with antibodies as indicated for 1 h at room temperature. Cells were then washed three times with PBS before detection with Alexa-488 or Alexa-555-conjugated anti-rabbit or anti-mouse antibodies (Molecular Probes). After washing in PBS and water, cells were mounted in Mowiol (100 mM Tris-HCl at pH 8.5, 10% (w/v) Mowiol (Calbiochem, San Diego, Calif.) and 25% (v/v) glycerol containing antifade (2.5% (w/v) 1,4-diazadicyclo-2.2.2-octane (Sigma)). Slides were examined using Zeiss inverted fluorescence microscope or a confocal laser scanning microscope (Axioplan 2 with LSM 510; Carl Zeiss Inc., Jena, Germany) equipped with 63×/1.4 Plan-Apochromat oil immersion objectives. Confocal images represent a single z-section of approximately 1.0 μm. Cytosolic microinjections with 1 mM FDP (Molecular probes) and 1 mg/ml of peptide in PBS were performed on Hela cells cultured on glass-bottom 3 cm plates. Fluorescence images from live cells were taken with identical settings and intensities were quantified using Zeiss Axioplan4 software.

Cell Growth and Soft Agar Assays 96-well plates were coated with BSA or matrix as indicated. Cells were seeded to the wells at $10^4$/well. TAT-peptides (α1-TAT fitc-YGRKKRRQRRRWKLG-FFKRPLKKKMEK (SEQ ID NO:2), Scr-TAT fitc-YGRKKRRQRRRLKGWRFKLKPKFKEMK (SEQ ID NO:2); Genemed Synthesis) and EGF (Sigma) were added as indicated and number of viable cells was detected with WST-1 (Roche) according to manufacturers protocol. Soft agar assays were performed as described[14]. Medium containing 200 nM TAT peptide were replaced every 48 h and after 9 days incubation, cultures were photographed double-blindly. Number and size of colonies from each field of view (4× magnification) we analysed using GeneTools software from Syngene. Colonies were classified according to size (small=200-499 pixels, medium=500-1000 and large over 1000).

Mice and Tumor Cell Inoculation

Male, pathogen-free nude mice were used when they were 4 weeks of age. HT1080 tumor cells (5×$10^6$ cells per 100 μl of PBS) were injected subdermally into the right dorsalateral flank of nude mice. Mice were treated with subdermal injections adjacent to the tumor cell inoculation site (20 μl of PBS, 20 μM α1-TAT or 20 μM Scr-TAT peptide in PBS) three times a week for the duration of the experiment. Mice were sacrificed 4 weeks after inoculation. The tumors were removed, their size quantified and processed into paraffin blocks for immunohistochemistry. IHC was preformed as described previously (Grant D. S. et al., Int. J. Cancer 2003 104:121-129).

Results:

To characterize signalling pathways activated by α1 integrin-mediated cell adhesion to collagen, we used the yeast two-hybrid system to identify proteins that interact with the α1 cytoplasmic domain (α1cyt). One of the positive clones encoded a 45 kDa form of TCPTP[15]. This molecule is a ubiquitously expressed nuclear non-receptor protein tyrosine phosphatase capable of translocating to the cytoplasm in response to mitogenic stimuli[11].

To verify the novel interaction in human cells, we first studied whether endogenous α1 integrin and TCPTP colocalize. PC3 and HeLa cells were plated onto different matrix proteins and α1-integrin and TCPTP were visualized by two-color immunofluorescence stainings. In cells plated on poly-L-lysine, which fails to activate integrins, TCPTP seemed both cytoplasmic and nuclear. In cells plated on fibronectin, which binds to integrins other than the four collagen-binding integrins, TCPTP was found diffusely in the cytosol (FIG. 1B). In contrast, upon adhesion to collagen TCPTP co-localized with the α1β1 integrin in peripheral areas of the cell membrane (FIG. 1A,B). These data show that endogenous integrin α1 and TCPTP co-localize in human cells specifically upon cell adhesion to collagen.

Previous work has shown, that TCPTP translocates from the nucleus in response to mitogenic stimuli[11] by a molecularly uncharacterized mechanism. As cell adhesion to collagen induced the co-localization of α1-integrin and TCPTP, we tested whether binding to matrix or mitogenic stimuli would induce physical association of the two proteins. In immunoprecipitation experiments, endogenous integrin α1β1 associated with endogenous TCPTP in HeLa cells following adhesion to collagen or serum stimulation while no interaction was detected in cells plated on poly-L-lysine or maintained in serum-free conditions (FIG. 1C). In addition, TCPTP failed to associate with fibronectin-binding integrins α5 and α6 in these cells even following serum stimulation (FIG. 1C). In reciprocal immunoprecipitation experiments, TCPTP readily bound to integrin a α1β1 but again specifically only following adhesion to collagen or serum induction (FIG. 1D). We conclude that endogenous α1 integrin and TCPTP become physically associated in response to collagen or mitogenic stimuli in human cells, thus providing the molecular explanation for TCPTP translocation to the plasma membrane.

HeLa cells have a high level of α1β1 surface expression (225±23 FACS mean fluorescence), significantly less α2β1 integrin (58.5±10.4 FACS mean fluorescence) and according to RT-PCR, no detectable α10 or α11 integrin. To study the specificity of the interaction between TCPTP and the collagen-binding integrins expressed in Hela cells, we performed pull-down experiments. Importantly, in pull-downs with GST-fused cytoplasmic tails of α1-(GST-cytα$_1$ and a2-integrins (GST-cytα2 from HeLa lysates, only GST-cytα1 was found to associate with endogenous TCPTP (FIG. 1E). Furthermore, the interaction is direct since purified recombinant TCPTP associates with GST-α1cyt but not with GST-α2cyt (FIG. 1F). The pull-down experiments further showed that the interaction between α1cyt and TCPTP involves the non-conserved amino acids in α1cyt, since a soluble synthetic peptide lacking the conserved Trp-Lys-Ile-Gly-Phe-Phe-sequence (SEQ ID NO:9) shared with all integrin α-subunits, was able to compete with α1cyt for the association with TCPTP (FIG. 1F). These data show that interaction between TCPTP and integrins is direct and specific to α1β1 integrin.

Overexpression studies have shown that TCPTP has several plasma membrane associated substrates such as EGFR[11], the insulin receptor[16] and Janus kinases (JAKs)[17] that regulate mitogen- and cytokine-induced signalling. In vitro studies, using proteolytically cleaved fragments of TCPTP, have proposed that the catalytic activity of TCPTP is regulated by an intramolecular inhibition involving a carboxy-terminal segment of the 45 kDa form of TCPTP[18]. However, it has remained unclear whether such a regulatory mechanism would function in cells and how it would operate. Since α1cyt and the carboxy-terminal segment of TCPTP both share a similar basic charge, we hypothesized that association of TCPTP with α1cyt could alleviate this autoinhibition by competition and lead to activation of the phosphatase. Indeed, cell adhesion to collagen induced catalytic activity of ectopically expressed TCPTP by 2.4 fold when compared to cells adhering to poly-L-lysine (FIG. 1G). Furthermore, following treatment with synthetic peptide having the sequence of the cytoplasmic tail of a1, the catalytic activity of immunoprecipitated TCPTP increased 2.95±0.48 fold (FIG. 2A), whereas the corresponding α2 tail peptide had no effect. The activation is specific, since another protein tyrosine phosphatase, SHP-2, was not activated by either peptide. Recombinant, purified TCPTP was highly activated with very low amounts of synthetic α1 tail peptide (FIG. 2B). To explore the molecular basis of α1cyt induced activation of TCPTP in more detail, recombinant, purified GST-TCPTP deletion mutants (FIG. 2C) were tested for their ability to interfere with the α1 cytoplasmic peptide induced activation of the full-length TCPTP (FIG. 2D). Deletion mutant 1 containing the amino-terminal half of TCPTP efficiently prevented the activation. In contrast, no competition was observed if only the most amino-terminal part was included, or if the amino-terminal half was deleted. Thus, integrin α1 cytoplasmic tail might associate with the amino-terminal part of TCPTP and activate it possibly by inhibiting the proposed autoregulatory carboxy-terminal segment[18] from interacting with the N-terminal part of the protein.

Integrin and growth factor mediated signals overlap and even synergize[2]. Cell adhesion to matrix, in particular, conveys permissive signals enabling efficient signalling through receptor tyrosine kinases. Furthermore, integrins associate with EGFR and induce its phosphorylation. EGFR is also a substrate for TCPTP and overexpression of the phosphatase has been shown to suppress EGFR phosphorylation and signalling[19] If integrin α1β1-mediated cell adhesion indeed activates TCPTP in vivo, EGFR may be affected. We therefore studied the effects of cell adhesion to matrix on EGFR phosphorylation. Serum-starved HeLa cells, either maintained as a monolayer on plastic or plated on collagen for 1 h, were treated with EGF for 5 minutes and analyzed for EGFR phosphorylation. EGF efficiently induced EGFR phosphorylation on all the tyrosine residues studied in cells maintained on plastic. In contrast, on collagen EGF-induced receptor phosphorylation was strongly inhibited (FIG. 3A). Adhesion to collagen attenuated most effectively the early EGF-induced peak of EGFR phosphorylation (FIG. 3B). To confirm that the effect was specifically due to integrin-collagen interactions and not a general phenomenon related to detachment and replating to matrix, EGF stimulation was performed on HeLa cells plated on either collagen or fibronectin. EGF-induced receptor phosphorylation was notably higher in cells on fibronectin than on collagen (FIG. 3C), suggesting that collagen binding integrins are specifically involved in the inhibition of EGF signalling.

We then determined to study whether collagen-induced inhibition of EGFR phosphorylation is mediated through the activation of TCPTP. Small interfering RNAs (siRNA) specific for TCPTP, but not scrambled control siRNA, efficiently reduced endogenous expression of TCPTP in HeLa cells (FIG. 3D). They also caused a significant increase in EGF-induced EGFR phosphorylation in cells plated on collagen (FIG. 3D). These knockdown experiments confirm a role for TCPTP in the collagen-induced inhibition of EGFR signalling.

HeLa cells can adhere to collagen with α1β1 as well as with α2β1 integrins. To study the integrin specificity of the integrin-TCPTP-EGFR signalling pathway, we used three strategies. First, in HT1080 fibrosarcoma cells, which do not express α1β1 integrin, adhesion to collagen failed to inhibit EGFR phosphorylation (FIG. 2E). Importantly, HT1080 cells transfected to transiently express α1 integrin, became sensitive to collagen-induced inhibition of EGFR phosphorylation (FIG. 2F). Secondly, in adherent, serum-starved HeLa cells, clustering of integrin α1-subunits with a monoclonal antibody, increased cytosolic PTP activity 1.5 fold and blocked EGF-induced phosphorylation of EGFR (FIG. 2G). Finally, we studied the specificity by using mouse embryonic fibroblasts derived form α1 integrin null mice and their wild type littermates[7]. Both the wild type and the $\alpha_1$-/-cells adhere to collagen ([9], FIG. 3E). However, in the absence of α1β1 integrin, TCPTP was not recruited to sites of adhesion, whereas in the wild type cells integrin α1β1 and TCPTP co-localized in adhesion sites at the periphery of the cell (FIG. 3E). α1-/- cells showed equivalent EGF-induced EGFR phosphorylation when plated on collagen or fibronectin, while in the wild type cells adhesion to collagen resulted in inhibition of EGF-induced signalling (FIG. 3F). Taken together, these experiments confirm that α1-integrin specifically activates TCPTP and this interaction leads to inhibited phosphorylation of EGFR.

Overexpression studies using mutant or wild-type forms of TCPTP have demonstrated its role in the regulation of cell proliferation[20]-23. Furthermore, TCPTP has been shown to suppress proliferation and anchorage-independent growth of glioblastoma cells expressing a mutant EGFR[23]. However, thus far the regulation of TCPTP activity and therefore the mechanism of the in vivo execution of its inhibitory function have been unknown. We showed here that integrin α1 cytoplasmic tail is capable of activating TCPTP in vitro. To test whether it induces phosphatase activity also in cells, we microinjected non-fluorescent diphosphofluorescein (FDP) into HeLa cells together with either α1 or α2 cytoplasmic tail peptides. FDP becomes fluorescent upon dephosphorylation and thus allows us to follow phosphatase activity in live HeLa cells. These quantitative assays clearly showed that integrin α1 cytoplasmic peptide induced phosphatase activity in HeLa cells when compared with the α2 or PBS co-injected cells (FIG. 4A).

Induction of phosphatase activity may influence tumorigenity of cells in a manner similar to overexpression of TCPTP[23]. Recently, the protein transduction domain of HIV transcriptional transactivator (TAT) protein, has been used to transport peptides and proteins into living cells[24,25]. Therefore, we used cell-permeable FITC-conjugated peptides fused to the TAT-protein to deliver α1-cyt peptide into cells for proliferation and tumorigenity assays. α1cyt-TAT peptide and a scramble control peptide both entered the cells efficiently (FIG. 4B), fluorescence was sustained over 24 hours and no detachment of cells was observed (not shown). In HeLa cells growing in 5% serum in suspension, 200 nM α1-TAT peptide inhibited serum-induced cell growth (FIG. 4B). In contrast, growth was not significantly altered by the control peptide. Furthermore, α1-TAT peptide was efficient in inhibiting EGF-induced cell growth while it had no effect on the basal growth and survival of HeLa cells maintained in serum-free conditions in suspension (FIG. 4D). Serum-induced growth of tumorigenic B104-1-1 cells (3T3 fibroblasts transformed with neu-oncogene) was also inhibited by α1-TAT peptide (FIG. 4C). Interestingly, α1-TAT peptide was effective only in regulating anchorage-independent, EGF-driven growth, since proliferation of adherent HeLa cells was not influenced (FIG. 3G). In addition, formation of large tumor colonies by HeLa cells cultured in soft-agar for 9 days was significantly inhibited by α1-TAT peptide, while the control peptide failed to significantly reduce colony size (FIG. 4D). Finally, growth of human fibrosarcoma cells as subcutaneous tumors in mice in vivo, was inhibited by treatment with the α1-TAT peptide (FIG. 5A). Interestingly, detailed immunohistochemical studies revealed that tumors treated with α1-TAT peptide showed more necrosis than the control tumors treated with either PBS injections of Scr-TAT (FIG. 5B). These experiments demonstrate that in vivo induction of phosphatase activity by α1 cytoplasmic tail peptide causes identical effects to those achieved by overexpressing TCPTP in tumorigenic cells[20,23]. Moreover, the peptide can be transduced to living cells and it efficiently blocks anchorage-independent, EGF-induced proliferation of malignant cells suggesting a possible role for α1-delivered negative signals in maintaining normal cell growth in vivo.

α-cytoplasmic domains of integrins are essential in regulating integrin-mediated biological responses[26], but only a few interacting proteins have been identified so far. Integrins are known to positively regulate receptor tyrosine kinase signalling and even trigger RTK activation in the absence of ligands[3,27] Also the ubiquitously expressed integrin α1 has been shown to activate ERK MAP-kinase pathway in primary cells in response to collagen[9]. On the other hand it seems to be down-regulated in breast cancer, ovarian cancer and lung adenocarcinoma[3,27,28]. The negative regulation of EGFR signalling via integrin a α1β1 mediated activation of TCPTP, seems to be a novel mechanism in adhesion mediated control of cellular responses. These findings provide molecular explanation for the control of phosphatase activity of this tumor suppressor protein in cells, and demonstrate one mechanism why TCPTP (like other PTPs) are promiscuous as isolated proteins, but highly specific in cells[29]. Local regulation of TCPTP by integrin α1 is likely to be important for other signalling pathways as well, where precise localized control of protein phosphorylation-dephosphorylation balance is essential. For example, the localized activation of TCPTP by interaction with integrin α1 cytoplasmic domain at the plasma membrane in close proximity with EGFR (that associates with integrins[27]) is a powerful way for cells to control RTK signalling in a tightly regulated manner. The inhibition of anchorage-independent but not adherent growth of cells by delivering α1 cytoplasmic peptide into living cells, may offer new means to target transformed cells. In conclusion, the negative regulation of EGFR signalling via integrin α1β1 mediated activation of a tumor suppressor protein is a novel paradigm in adhesion-mediated control of cellular responses.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

BIBLIOGRAPHY

1. Hynes, R. O. Integrins: bidirectional, allosteric signaling machines. *Cell* 110, 673-87 (2002).
2. Miyamoto, S., Teramoto, H., Gutkind, J. S. & Yamada, K. M. Integrins can collaborate with growth factors for phosphorylation of receptor tyrosine kinases and MAP kinase activation: roles of integrin aggregation and occupancy of receptors. *J Cell Biol* 135, 1633-42 (1996).
3. Moro, L. et al. Integrins induce activation of EGF receptor: role in MAP kinase induction and adhesion-dependent cell survival. *Embo J* 17, 6622-32 (1998).
4. Ivaska, J. et al. Integrin alpha 2 beta 1 promotes activation of protein phosphatase 2A and dephosphorylation of Akt and glycogen synthase kinase 3 beta. *Mol Cell Biol* 22, 1352-9 (2002).

5. Howe, A., Aplin, A. E., Alahari, S. K. & Juliano, R. L. Integrin signaling and cell growth control. *Curr Opin Cell Biol* 10, 220-31 (1998).
6. Ivaska, J. et al. Integrin alpha2beta1 mediates isoform-specific activation of p38 and upregulation of collagen gene transcription by a mechanism involving the alpha2 cytoplasmic tail. *J Cell Biol* 147, 401-16 (1999).
7. Gardner, H., Kreidberg, J., Koteliansky, V. & Jaenisch, R. Deletion of integrin alpha 1 by homologous recombination permits normal murine development but gives rise to a specific deficit in cell adhesion. *Dev Biol* 175, 301-13 (1996).
8. Wary, K. K., Mainiero, F., Isakoff, S. J., Marcantonio, E. E. & Giancotti, F. G. The adaptor protein Shc couples a class of integrins to the control of cell cycle progression. *Cell* 87, 733-43 (1996).
9. Pozzi, A., Wary, K. K., Giancotti, F. G. & Gardner, H. A. Integrin alpha1beta1 mediates a unique collagen-dependent proliferation pathway in vivo. *J Cell Biol* 142, 587-94 (1998).
10. Loster, K., Vossmeyer, D., Hofmann, W., Reutter, W. & Danker, K. alpha1 Integrin cytoplasmic domain is involved in focal adhesion formation via association with intracellular proteins. *Biochem J* 356, 233-40 (2001).
11. Tiganis, T., Bennett, A. M., Ravichandran, K. S. & Tonks, N. K. Epidermal growth factor receptor and the adaptor protein p52Shc are specific substrates of T-cell protein tyrosine phosphatase. *Mol Cell Biol* 18, 1622-34 (1998).
12. Ivaska, J., Whelan, R. D., Watson, R. & Parker, P. J. PKC epsilon controls the traffic of beta1 integrins in motile cells. *Embo J* 21, 3608-19 (2002).
13. Ivaska, J., Bosca, L. & Parker, P. J. PKCepsilon is a permissive link in integrin-dependent IFN-gamma signalling that facilitates JAK phosphorylation of STAT1. *Nat Cell Biol* 5, 363-9 (2003).
14. Kim, T. Y. et al. Oncogenic potential of a dominant negative mutant of interferon regulatory factor 3. *J Biol Chem* 278, 15272-8 (2003).
15. Mosinger, B., Jr., Tillmann, U., Westphal, H. & Tremblay, M. L. Cloning and characterization of a mouse cDNA encoding a cytoplasmic protein-tyrosine-phosphatase. *Proc Natl Acad Sci USA* 89, 499-503 (1992).
16. Galic, S. et al. Regulation of insulin receptor signaling by the protein tyrosine phosphatase TCPTP. *Mol Cell Biol* 23, 2096-108 (2003).
17. Simoncic, P. D., Lee-Loy, A., Barber, D. L., Tremblay, M. L. & McGlade, C. J. The T cell protein tyrosine phosphatase is a negative regulator of janus family kinases 1 and 3. *Curr Biol* 12, 446-53 (2002).
18. Hao, L., Tiganis, T., Tonks, N. K. & Charbonneau, H. The noncatalytic C-terminal segment of the T cell protein tyrosine phosphatase regulates activity via an intramolecular mechanism. *J Biol Chem* 272, 29322-9 (1997).
19. Tiganis, T., Kemp, B. E. & Tonks, N. K. The protein-tyrosine phosphatase TCPTP regulates epidermal growth factor receptor-mediated and phosphatidylinositol 3-kinase-dependent signaling. *J Biol Chem* 274, 27768-75 (1999).
20. Mitra, S. K. & Swarup, G. Inhibition of anchorage-independent cell growth, adhesion, and cyclin D1 gene expression by a dominant negative mutant of a tyrosine phosphatase. *Exp Cell Res* 270, 32-44 (2001).
21. Cool, D. E. et al. Cytokinetic failure and asynchronous nuclear division in BHK cells overexpressing a truncated protein-tyrosine-phosphatase. *Proc Natl Acad Sci USA* 89, 5422-6 (1992).
22. Cool, D. E., Tonks, N. K., Charbonneau, H., Fischer, E. H. & Krebs, E. G. Expression of a human T-cell protein-tyrosine-phosphatase in baby hamster kidney cells. *Proc Natl Acad Sci USA* 87, 7280-4 (1990).
23. Klingler-Hoffmann, M. et al. The protein tyrosine phosphatase TCPTP suppresses the tumorigenicity of glioblastoma cells expressing a mutant epidermal growth factor receptor. *J Biol Chem* 276, 46313-8 (2001).
24. Denicourt, C. & Dowdy, S. F. Protein transduction technology offers novel therapeutic approach for brain ischemia. *Trends Pharmacol Sci* 24, 216-8 (2003).
25. Leifert, J. A. & Whitton, J. L. "Translocatory proteins" and "protein transduction domains": a critical analysis of their biological effects and the underlying mechanisms. *Mol Ther* 8, 13-20 (2003).
26. Liu, S., Calderwood, D. A. & Ginsberg, M. H. Integrin cytoplasmic domain-binding proteins. *J Cell Sci* 113 (Pt 20), 3563-71 (2000).
27. Moro, L. et al. Integrin-induced epidermal growth factor (EGF) receptor activation requires c-Src and p130Cas and leads to phosphorylation of specific EGF receptor tyrosines. *J Biol Chem* 277, 9405-14 (2002).
28. Su, A. I. et al. Molecular classification of human carcinomas by use of gene expression signatures. *Cancer Res* 61, 7388-93 (2001).
29. Flint, A. J., Tiganis, T., Barford, D. & Tonks, N. K. Development of "substrate-trapping" mutants to identify physiological substrates of protein tyrosine phosphatases. *Proc Natl Acad Sci USA* 94, 1680-5 (1997).

The invention claimed is:

1. A method for activation of T cell protein tyrosine phosphatase (TCPTP) in an individual, the said method comprising administering to an individual in need thereof an effective amount of a peptide consisting of the amino acid sequence RPLKKKMEK (SEQ ID NO: 1).

2. The method according to claim 1 wherein the peptide is administered as the peptide or as a cell membrane permeable fusion protein.

3. The method according to claim 2 wherein the fusion protein comprises a protein transduction domain of HIV transcriptional transactivator (TAT) protein and the amino acid sequence RPLKKKMEK (SEQ ID NO:1).

4. The method according to claim 1 wherein the activation of TCPTP in the individual inhibition of tyrosine kinase signalling in the individual.

5. The method according to claim 4 wherein the tyrosine kinase is selected from the group consisting of an epidermal growth factor receptor (EGFR), an insulin receptor and a Janus kinase.

6. The method according to claim 4 wherein the peptide is administered as the peptide or as a cell membrane permeable fusion protein.

7. The method according to claim 6 wherein the fusion protein comprises a protein transduction domain of HIV transcriptional transactivator (TAT) protein and the amino acid sequence RPLKKKMEK (SEQ ID NO:1).

8. The method according to claim 4 wherein the inhibition of tyrosine kinase signalling in the individual effects the treatment of a disease or disorder in the individual, wherein the disease or disorder is one which can be treated by inhibiting tyrosine kinase signalling in the individual.

9. The method according to claim 8 wherein the tyrosine kinase is selected from the group consisting of an epidermal growth factor receptor (EGFR), an insulin receptor and a Janus kinase.

10. The method according to claim 8 wherein the disease is a cancer selected from the group consisting of fibrosarcoma and cervical cancer.

11. The method according to claim 8 wherein the peptide is administered as the peptide or as a cell membrane permeable fusion protein.

12. The method according to claim 11 wherein the fusion protein comprises a protein transduction domain of HIV transcriptional transactivator (TAT) protein and the amino acid sequence RPLKKKMEK (SEQ ID NO:1).

13. The method according to claim 10 wherein the peptide is administered as the peptide or as a cell membrane permeable fusion protein.

14. The method according to claim 13 wherein the fusion protein comprises a protein transduction domain of HIV transcriptional transactivator (TAT) protein and the amino acid sequence RPLKKKMEK (SEQ ID NO:1).

15. A method for activation of T cell protein tyrosine phosphatase (TCPTP) in an individual comprising administering to an individual in need thereof an effective amount of a peptide selected from the group consisting of (i) a peptide consisting of the amino acid sequence RPLKKKMEK (SEQ ID NO:1) and (ii) a cell membrane permeable fusion protein, wherein the C terminus of said fusion protein consists of the amino acid sequence RPLKKKMEK (SEQ ID NO:1).

\* \* \* \* \*